(12) United States Patent
Bolli et al.

(10) Patent No.: US 7,452,896 B2
(45) Date of Patent: Nov. 18, 2008

(54) PYRIMIDINE-SULFAMIDES AND THEIR USE AS ENDOTHELIAN RECEPTOR ANTAGONIST

(75) Inventors: Martin Bolli, Allschwil (CH);
Christoph Boss, Allschwil (CH);
Martine Clozel, Binningen (CH);
Walter Fischli, Allschwil (CH); Thomas Weller, Binningen (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 524 days.

(21) Appl. No.: 10/537,400

(22) PCT Filed: Nov. 10, 2003

(86) PCT No.: PCT/EP03/12502

§ 371 (c)(1),
(2), (4) Date: Jun. 2, 2005

(87) PCT Pub. No.: WO2004/050640

PCT Pub. Date: Jun. 17, 2004

(65) Prior Publication Data

US 2007/0167472 A1    Jul. 19, 2007

(30) Foreign Application Priority Data

Dec. 2, 2002    (EP) .................... 0213601

(51) Int. Cl.
*C07D 239/46* (2006.01)
*A61K 31/505* (2006.01)

(52) U.S. Cl. .................. 514/269; 544/296; 544/319

(58) Field of Classification Search .............. 544/296, 544/319; 514/269
See application file for complete search history.

(56) References Cited

U.S. PATENT DOCUMENTS 4,233,294 A    11/1980    Maurer et al.

FOREIGN PATENT DOCUMENTS

| EP | 0 658 548 B1 | 11/1997 |
|----|--------------|---------|
| EP | 0 633 259 B1 | 1/1999 |
| EP | 0 526 708 B1 | 10/2000 |
| EP | 0 882 719 B1 | 5/2001 |
| EP | 0 743 307 B1 | 9/2001 |
| EP | 0 959 072 B1 | 9/2002 |
| FR | 1549494 | 12/1968 |
| WO | WO-96/19459 | 6/1996 |
| WO | WO-02/053557 A1 | 7/2002 |

OTHER PUBLICATIONS

Simone, Oncology: Introduction, Cecil Textbook of Medicine, 20th Edition, vol. 1, pp. 1004-1010, 1996.*

Rubanyi et al., Endothelins: Molecular Biology, Biochemistry, Pharmacology, Physiology, and Pathophysiology, Pharmacological Reviews, vol. 46, No. 3, pp. 325-415, 1994.*

Volker Breu, et al.; "In vitro characterization of RO 46-2005, a novel synthetic non-peptide endothelin antagonist of $ET_A$ and $ET_B$ receptors"; FEBS 13244; vol. 334(2); Nov. 1993; pp. 210-214; On CD under filename Breu_20050526160232.pdf.

D. J. Brown, et al.; "Pyrimidine Reactions VI.* The Amination of Chloropyrimidines with n-Alkylamines"; Aust. J. Chem; 1964; 17, pp. 794-802; On CD as filename Brown_20050526162958.pdf.

Elliott Cohen, et al.; "Sulfamoyl Chloride, Sulfamides and Sulfimide"; J. Am. Chem. Soc.; 1962; vol. 84; pp. 1994-2002. On CD as filename Cohen_20050526162403.pdf.

Donald G. Crosby, et al.; "n-Butyl 5-Chloro-2-pyrimidoxyacetate-A Plant Growth Regulator Analog"; J. Org. Chem.; 1960; vol. 25; pp. 1916-1919. On CD as filename Crosby_20050526162918.pdf.

Georges Dewynter, et al.; "Synthese de 'sulfahydantoines' chirales. Aspects stereochimiques et protection regiospecifique."; Tetrahedron; 1993; vol. 49(1); pp. 65-76; On CD as filename Dewynter_20050526163615.pdf.

Roger P. Dickinson, et al.; "Thromboxane Modulating Agents. 3. 1H-Imidazol-1-yulalkyl- and 3-Pyridinylalkyl-Substituted 3-[2-[Arylsulfonyl)amino]ethyl]benzenepropanoic Acid Derivatives as Dual Thromboxane Synthase Inhibitor/Thromboxane Receptor Antagonists"; J. Med. Chem.; 1997; vol. 40; p. 3442. On CD as filename Dickinson_20050526162822.pdf.

Wolfgang, Gohring, et al.; "Development of a Process to Prepare 2-Cyanopyrimidine on Commercial Scale"; Chimia; 1996; vol. 50; pp. 538-543; On CD as filename Goehring_20050526160404.pdf.

Roderich Graf; "Umsetzungen mit N-Carbonyl-sulfamidsaurechlorid$^{1,2}$), I Uber das Sulfamidsaurechlorid"; 1959; vol. 92; p. 509; On CD as filename Graf_20050526162550.pdf.

Stig Andre Jacobsen, et al.; "Phenylation of pyrimidinones using diphenyliodonium salts"; J. Chem. Soc. Perkin Trans 1; 1999; pp. 3265-3268; On CD as filename Jacobsen_20050526163157.pdf.

Marc Julia, et al.; "Sur quelques hydroxy et methoxy-3 phenoxyethylamines chlorees analogues des tryptamines hallucinogenes"; Chim. Ther. 1965; vol. 4; pp. 334-343; On CD as filename Julia_20050526162250.pdf.

(Continued)

*Primary Examiner*—Deepak Rao
(74) *Attorney, Agent, or Firm*—Dickstein Shapiro LLP

(57) ABSTRACT

The invention relates to novel sulfamic acid amides of General Formula (I) and their use as active ingredients in the preparation of pharmaceutical compositions. The invention also concerns related aspects including processes for the preparation of the compounds, pharmaceutical compositions containing one or more of those compounds and especially their use as endothelin receptor antagonists.

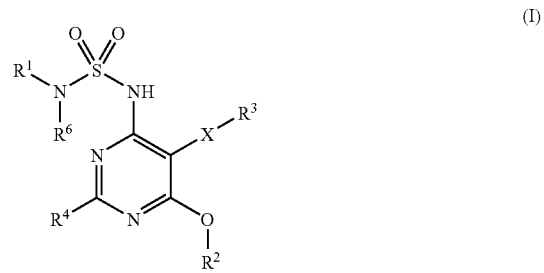

(I)

13 Claims, No Drawings

OTHER PUBLICATIONS

J. A. Kloek, et al.; "An Improved Synthesis of Sulfamoyl Chlorides"; J. Org. Chem; 1976; vol. 41; p. 4028; On CD as filename Kloek_20050526162645.pdf.

Yusuhisa Kohara, et al.; "Synthesis and Angiotensin II Receptor Antagonistic Activities of Benzimidazole Derivatives Bearing Acidic Heterocycles as Novel Tetrazole Bioisosteres"; J. Med. Chem; 1996; vol. 39; pp. 5228-5235; On CD as filename Kohara_20050526162200.pdf.

Henry C. Koppel, et al.; "Pyrimidines. X. (Antibiotics. II) Synthesis of Bacimethrin, 2-Methoxy Analog of Thiamine and Related Alkoxypyrimidines"; J. Org. Chem; 1962; vol. 27; pp. 3614-3617; On CD as filename Koppel_20050526163054.pdf.

C. Maggiali, et al.; "Effetti Anti $H_1$-Istaminici E Antimuscarinici Di Composti 2-E 4-[Benzil-(2-Dimetilaminoetil)Amino]Pirimidinici"; Farmaco, Ed. Sci.; 1988; vol. 43; pp. 277-292; On CD as filename Maggiali_20050526163243.pdf.

Jerry March; Advanced Organic Chemistry, 4$^{th}$ Edition; 1994; p. 499; On CD as filename March_20050526162122.pdf.

Marvin A. McMillen, et al.; "Endothelins: Polyfunctional Cytokines"; J. Am. Coll. Surg.; 1995; vol. 180; p. 621: On CD as filename McMillen_20050525104659.pdf.

E. D. Morgan; "Synthesis of p-Alkylphenylacetic Acids"; Tetrahedron; 1967; vol. 23; p. 1735; On CD as filename Morgan_20050526163434.pdf.

Werner Neidhart, et al.; "Discovery of RO 48-5695: A Potent Mixed Endothelin Receptor Antagonist Optimized From Bosentan"; Bioorg. Med. Chem. Lett.; 1997; vol. 7; pp. 2223-2228; On CD as filename Neidhart 2_20050526161918.pdf.

Werner Neidhart, et al.; "The Discovery of Nonpeptide Endothelin Receptor Angagonists. Progression towards Bosentan"; Chimia; vol. 50; pp. 519-524; On CD as filename Neidhart_20050526160756.pdf.

Richard A. Nugent, et al.; "Pyrimidine Thioethers: A Novel Class of HIV-1 Reverse Transcriptase Inhibitors with Activity Against BHAP-Resistant HIV"; J. Med. Chem.; 1998; vol. 41; pp. 3793-3803; On CD as filename Nugent_20050526162015.pdf.

Yoshihiro Ogawa, et al.; "Molecular Cloning of a Non-Isopeptide-Selective Human Endothelin Receptor"; BBRC; 1991; vol. 178; pp. 248-255; On CD as filename Ogawa_20050525110759.pdf.

Eliot H. Ohlstein, et al.; "Endothelin-1 Modulates Vascular Smooth Muscle Structure and Vasomotion: Implications in Cardiovascular Pathology"; Drug. Dev. Res.; 1993; vol. 29; pp. 108-128; On CD as filename Ohlstein_20050525110638.pdf.

Richard E. Olson, et al.; "Orally Active Isoxazoline Glycoprotein IIb/IIIa Antagonists with Extended Duration of Action"; J. Med. Chem.; 1999; pp. 1178-1192; On CD as filename Oslon_20050526162724.pdf.

G. M. Rubanyi, et al.; "Endothelins: Molecular Biology, Biochemistry, Pharmacology, Physiology, and Pathophysiology"; Pharmacol. Rev.; 1994; vol. 46(3); p. 328; On CD as filename Rubanyi_20050525105453.pdf.

Takeshi Sakurai, et al.; "Cloning of a cDNA encoding a non-isopeptide-selective subtype of the endothelin receptor"; Nature; 1990; vol. 348; p. 732; On CD as filename Sakurai_20050525110520.pdf.

Michael J. Sumner, et al.; "Endothelin ETA and ETB receptors mediate vascular smooth muscle contraction" Brit. J. Pharmacol.; 1992; vol. 107; p. 858; On CD as filename Sumner_20050526160142.pdf.

Matthew J. Tozer, et al.; "4-Chlorobenzyl Sulfonamide and Sulfamide Derivatives of Histamine Homologues: The Design of Potent Histamine $H_1$ Receptor Antagonists"; Bioorg. Med. Chem. Lett.; 1999; vol. 9; p. 3103; On CD as filename Tozer_20050526163521.pdf.

von Gunther Weiss, et al; "Herstellung und Reaktionen von N-Monoalkyl-amidosulfonylchloriden"; Leibigs Ann. Chem.; 1969; vol. 729; p. 40; On CD as filename Weiss_20050526162455.pdf.

Masashi Yanagisawa, et al.; "A novel potent vasoconstrictor peptide produced by vascular endothelial cells"; Nature; 1988; vol. 332; p. 411; On CD as filename Yanagisawa_20050525110419.pdf.

H. Arai, et al.; Nature; 1990; vol. 348; p. 730; Will be forwarded at a later date.

The International Search Report issued for the Parent PCT Application.

* cited by examiner

PYRIMIDINE-SULFAMIDES AND THEIR USE AS ENDOTHELIAN RECEPTOR ANTAGONIST

The present invention relates to novel pyrimidine-sulfamides of the general formula I and their use as active ingredients in the preparation of pharmaceutical compositions. The invention also concerns related aspects including processes for the preparation of the compounds, pharmaceutical compositions containing one or more compounds of the general formula I, and especially their use as endothelin receptor antagonists.

Endothelins (ET-1, ET-2, and ET-3) are 21-amino acid peptides produced and active in almost all tissues (Yanagisawa M et al.: Nature (1988) 332:411). Endothelins are potent vasoconstrictors and important mediators of cardiac, renal, endocrine and immune functions (McMillen M A et al.: J Am Coll Surg (1995) 180:621). They participate in bronchoconstriction and regulate neurotransmitter release, activation of inflammatory cells, fibrosis, cell proliferation and cell differentiation (Rubanyi GM et al.: Pharmacol Rev (1994) 46:328).

Two endothelin receptors have been cloned and characterized in mammals ($ET_A$, $ET_B$) (Arai H et al.: Nature (1990) 348:730; Sakurai T et al.: Nature (1990) 348:732). The $ET_A$ receptor is characterized by higher affinity for ET-1 and ET-2 than for ET-3. It is predominant in vascular smooth muscle cells and mediates vasoconstricting and proliferative responses (Ohlstein E H et al.: Drug Dev Res (1993) 29:108). In contrast, the $ET_B$ receptor has equivalent affinity for the three endothelin isopeptides and binds the linear form of endothelin, tetra-ala-endothelin, and sarafotoxin S6C (Ogawa Y et al.: BBRC (1991) 178:248). This receptor is located in the vascular endothelium and smooth muscles, and is also particularly abundant in lung and brain. The $ET_B$ receptor from endothelial cells mediates transient vasodilator responses to ET-1 and ET-3 through the release of nitric oxide and/or prostacyclin whereas the $ET_B$ receptor from smooth muscle cells exerts vasoconstricting actions (Sumner M J et al.: Brit J Pharmacol (1992) 107:858). $ET_A$ and $ET_B$ receptors are highly similar in structure and belong to the superfamily of G-protein coupled receptors.

A pathophysiological role has been suggested for ET-1 in view of its increased plasma and tissue levels in several disease states such as hypertension, pulmonary hypertension, sepsis, atherosclerosis, acute myocardial infarction, congestive heart failure, renal failure, migraine and asthma. As a consequence, endothelin receptor antagonists have been studied extensively as potential therapeutic agents. Endothelin receptor antagonists have demonstrated preclinical and/or clinical efficacy in various diseases such as cerebral vasospasm following subarachnoid hemorrhage, heart failure, pulmonary and systemic hypertension, neurogenic inflammation, renal failure and myocardial infarction.

Today, only one endothelin receptor antagonist (Tracleer™) is marketed and several are in clinical trials. However, some of these molecules possess a number of weaknesses such as complex synthesis, low solubility, high molecular weight, poor pharmacokinetics, or safety problems (e.g. liver enzyme increases). Furthermore, the contribution of differing $ET_A/ET_B$ receptor blockade to the clinical outcome is not known. Thus, tailoring of the physicochemical and pharmacokinetic properties and the selectivity profile of each antagonist for a given clinical indication is mandatory. So far, no endothelin receptor antagonists with a pyrimidine core structure containing a sulfamide unit, have been reported [2, 3, 5, 6, 8]. Surprisingly, we have discovered a new class of substituted pyrimidines of the structure below and found that they allow the specific tailoring described above and, in addition, compounds exhibiting mixed as well as $ET_A$-selective binding profiles have been identified.

The inhibitory activity of the compounds of general formula I on endothelin receptors can be demonstrated using the test procedures described hereinafter:

For the evaluation of the potency and efficacy of the compounds of the general formula I the following tests were used:

1) Inhibition of Endothelin Binding to Membranes from CHO Cells Carrying Human ET Receptors:

For competition binding studies, membranes of CHO cells expressing human recombinant $ET_A$ or $ET_B$ receptors were used. Microsomal membranes from recombinant CHO cells were prepared and the binding assay made as previously described (Breu V., et al, FEBS Lett 1993; 334:210).

The assay was performed in 200 uL 50 mM Tris/HCl buffer, pH 7.4, including 25 mM $MnCl_2$, 1 mM EDTA and 0.5% (w/v) BSA in polypropylene microtiter plates. Membranes containing 0.5 ug protein were incubated for 2 h at 20° C. with 8 pM [$^{125}$I]ET-1 (4000 cpm) and increasing concentrations of unlabelled antagonists. Maximum and minimum binding were estimated in samples without and with 100 nM ET-1, respectively. After 2 h, the membranes were filtered on filterplates containing GF/C filters (Unifilterplates from Canberra Packard S.A. Zürich, Switzerland). To each well, 50 uL of scintillation cocktail was added (MicroScint 20, Canberra Packard S.A. Zürich, Switzerland) and the filter plates counted in a microplate counter (TopCount, Canberra Packard S.A. Zürich, Switzerland).

All the test compounds were dissolved, diluted and added in DMSO. The assay was run in the presence of 2.5% DMSO which was found not to interfere significantly with the binding. $IC_{50}$ was calculated as the concentration of antagonist inhibiting 50% of the specific binding of ET-1. For reference compounds, the following $IC_{50}$ values were found: $ET_A$ cells: 0.075 nM (n=8) for ET-1 and 118 nM (n=8) for ET-3; $ET_B$ cells: 0.067 nM (n=8) for ET-1 and 0.092 nM (n=3) for ET-3.

The $IC_{50}$ values obtained with compounds of general formula I are given in Table 1.

TABLE 1

| Compound of Example | $IC_{50}$ [nM] | |
| --- | --- | --- |
| | $ET_A$ | $ET_B$ |
| Example 1 | 0.28 | 174 |
| Example 2 | 0.22 | 222 |
| Example 3 | 0.20 | 120 |
| Example 4 | 1.27 | 560 |

2) Inhibition of Endothelin-Induced Contractions on Isolated Rat Aortic Rings ($ET_A$ Receptors) and Rat Tracheal Rings ($ET_B$ Receptors):

The functional inhibitory potency of the endothelin antagonists was assessed by their inhibition of the contraction induced by endothelin-1 on rat aortic rings ($ET_A$ receptors) and of the contraction induced by sarafotoxin S6c on rat tracheal rings ($ET_B$ receptors). Adult Wistar rats were anesthetized and exsanguinated. The thoracic aorta or trachea were excised, dissected and cut in 3-5 mm rings. The endothelium/epithelium was removed by gentle rubbing of the intimal surface. Each ring was suspended in a 10 ml isolated organ bath filled with Krebs-Henseleit solution (in mM; NaCl 115, KCl 4.7, $MgSO_4$ 1.2, $KH_2PO_4$ 1.5, $NaHCO_3$ 25, $CaCl_2$ 2.5, glucose 10) kept at 37° C. and gassed with 95% $O_2$ and 5% $CO_2$. The rings were connected to force transducers and isometric tension was recorded (EMKA Technologies SA, Paris, France). The rings were stretched to a resting tension of 3 g (aorta) or 2 g (trachea). Cumulative doses of ET-1 (aorta) or sarafotoxin S6c (trachea) were added after a 10 min incubation with the test compound or its vehicle. The functional inhibitory potency of the test compound was assessed by calculating the concentration ratio, i.e. the shift to the right of the $EC_{50}$ induced by different concentrations of test compound. $EC_{50}$ is the concentration of endothelin needed to get a half-maximal contraction, $pA_2$ is the negative logarithm of the antagonist concentration which induces a two-fold shift in the $EC_{50}$ value.

The $pA_2$ values obtained with compounds of formula I are given in Table 2.

TABLE 2

| | $pA_2$ value | |
|---|---|---|
| Compound of Example | Aorta | Trachea |
| Example 1 | 6.90 | 5.29 |
| Example 2 | 8.48 | <5.0 |

Because of their ability to inhibit the endothelin binding, the described compounds can be used for treatment of diseases, which are associated with an increase in vasoconstriction, proliferation or inflammation due to endothelin. Examples of such diseases are hypertension, pulmonary hypertension, coronary diseases, cardiac insufficiency, renal and myocardial ischemia, renal failure, cerebral ischemia, dementia, migraine, subarachnoidal hemorrhage, Raynaud's syndrome, digital ulcers and portal hypertension. They can also be used in the treatment or prevention of atherosclerosis, restenosis after balloon or stent angioplasty, inflammation, stomach and duodenal ulcer, cancer, melanoma, prostate cancer, prostatic hypertrophy, erectile dysfunction, hearing loss, amaurosis, chronic bronchitis, asthma, pulmonary fibrosis, gram negative septicemia, shock, sickle cell anemia, glomerulonephritis, renal colic, glaucoma, connective tissue diseases, therapy and prophylaxis of diabetic complications, complications of vascular or cardiac surgery or after organ transplantation, complications of cyclosporin treatment, pain, hyperlipidemia as well as other diseases, presently known to be related to endothelin.

The compounds can be administered orally, rectally, parenterally, e.g. by intravenous, intramuscular, subcutaneous, intrathecal or transdermal administration or sublingually or as ophthalmic preparation or administered as aerosol. Examples of applications are capsules, tablets, orally administered suspensions or solutions, suppositories, injections, eye-drops, ointments or aerosols/nebulizers.

Preferred applications are intravenous, intramuscular, or oral administrations as well as eye drops. The dosage used depends upon the type of the specific active ingredient, the age and the requirements of the patient and the kind of application. Generally, dosages of 0.1-50 mg/kg body weight per day are considered. The preparations with compounds can contain inert or as well pharmacodynamically active excipients. Tablets or granules, for example, could contain a number of binding agents, filling excipients, carrier substances or diluents.

The present invention relates to pyrimidine-sulfamides of the general formula I,

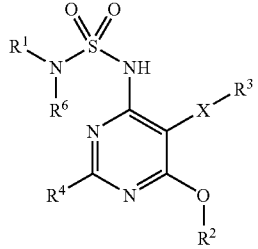

General Formula I wherein
$R^1$ represents lower alkyl-O—$CH_2$)$_n$—, cycloalkyl-O—($CH_2$)$_n$—, cycloalkyl-$CH_2$—O—($CH_2$)$_n$—;
$R^2$ represents —$CH_3$; $R^a$—Y—($CH_2$)$_m$—;
$R^3$ represents aryl; heteroaryl;
$R^4$ represents hydrogen; trifluoromethyl; lower alkyl; lower alkyl-amino; lower alkyloxy; lower alkyloxy-lower alkyloxy; hydroxy-lower alkyloxy; lower alkyl-sulfinyl; lower alkylthio; lower alkylthio-lower alkyl; hydroxy-lower alkyl; lower alkyloxy-lower alkyl; hydroxy-lower alkyloxy-lower alkyl; hydroxy-lower alkylamino; lower alkylamino-lower alkyl; amino; di-lower alkylamino; [N-(hydroxy-lower alkyl)-N-(lower alkyl)]-amino; aryl; arylamino; aryl-lower alkylamino; arylthio; aryl-lower alkylthio; aryloxy; aryl-lower alkyloxy; aryl-lower alkyl; arylsulfinyl; heteroaryl; heteroaryloxy; heteroarylamino; heteroarylthio; heteroaryl-lower alkyl; heteroaryl-sulfinyl; heterocyclyl; heterocyclyl-lower alkyloxy; heterocyclyloxy; heterocyclyl-amino; heterocyclyl-lower alkylamino; heterocyclylthio; heterocyclyl-lower alkyl-thio; heterocyclyl-lower alkyl; heterocyclylsulfinyl; cycloalkyl; cycloalkyloxy; cycloalkyl-lower alkyloxy; cycloalkylamino; cycloalkyl-lower alkylamino; cycloalkyl-thio; cycloalkyl-lower alkylthio; cycloalkyl-lower alkyl; cycloalkylsulfinyl;
$R^6$ represents hydrogen or methyl;
X represents oxygen; sulfur; —$CH_2$— or a bond;
Y represents a bond, —O—; —NH—; —$SO_2$—NH—; —NH—$SO_2$—NH—; —O—CO—; —CO—O—; —O—CO—NH—; —NH—CO—O—; —NH—CO—NH—;
n represents the integers 2, 3, or 4;
m represents the integers 2, 3, or 4;
$R^a$ represents aryl, heteroaryl, lower alkyl, cycloalkyl, hydrogen;

and optically pure enantiomers, mixtures of enantiomers such as for example racemates, optically pure diastereomers, mixtures of diastereomers, diastereomeric racemates, mixtures of diastereomeric racemates and the meso-forms and pharmaceutically acceptable salts thereof.

In the definitions of the general formula I—if not otherwise stated—the expression lower means straight and branched chain groups with one to seven carbon atoms, preferably 1 to 4 carbon atoms. Examples of lower alkyl and lower alkoxy groups are methyl, ethyl, n-propyl, isopropyl, n-butyl, isobutyl, sec.-butyl, tert.-butyl, pentyl, hexyl, heptyl, methoxy, ethoxy, propoxy, butoxy, iso-butoxy, sec.-butoxy and tert.-butoxy. Lower alkylendioxy-groups are preferably methylendioxy and ethylen-dioxy groups. Examples of lower alkanoyl-groups are acetyl, propanoyl and butanoyl. Lower alkenylen means e.g. vinylen, propenylen and butenylen. Lower alkenyl and lower alkynyl means groups like ethenyl, propenyl, butenyl, 2-methyl-propenyl, and ethinyl, propinyl, butinyl, pentinyl, 2-methyl-pentinyl. Lower alkenyloxy means allyloxy, vinyloxy and propenyloxy. The expression cycloalkyl means a saturated cyclic hydrocarbon ring with 3 to 7 carbon atoms, e.g. cyclopropyl, cyclobutyl, cyclopentyl, cyclohexyl and cycloheptyl, which may be substituted with lower alkyl, hydroxy-lower alkyl, amino-lower alkyl, and lower alkoxy-lower alkyl groups. The expression heterocyclyl means saturated or unsaturated (but not aromatic), four, five-, six- or seven-membered rings containing one or two nitrogen, oxygen or sulfur atoms which may be the same or different and which rings may be adequately substituted with lower alkyl, lower alkoxy, e.g. piperidinyl, morpholinyl, thiomorpholinyl, piperazinyl, tetrahydropyranyl, dihydropyranyl, 1,4-dioxanyl, pyrrolidinyl, tetrahydrofuranyl, dihydropyrrolyl, dihydroimidazolyl, dihydropyrazolyl, pyrazolidinyl and substituted derivatives of such rings with substituents as outlined above. The expression heteroaryl means six-membered aromatic rings containing one to four nitrogen atoms, benzo-fused six-membered aromatic rings containing one to three nitrogen atoms, five-membered aromatic rings containing one oxygen or one nitrogen or one sulfur atom, benzo-fused five-membered aromatic rings containing one oxygen or one nitrogen or one sulfur atom, five membered aromatic rings containing an oxygen and nitrogen atom and benzo-fused derivatives thereof, five membered aromatic rings containing a sulfur and a nitrogen atom and benzo fused derivatives thereof, five-membered aromatic rings containing two nitrogen atoms and benzo fused derivatives thereof, five membered aromatic rings containing three nitrogen atoms and benzo fused derivatives thereof or the tetrazolyl ring; e.g. furanyl, thienyl, pyrrolyl, pyridinyl, pyrimidinyl, indolyl, quinolinyl, isoquinolinyl, imidazolyl, triazinyl, thiazinyl, thiazolyl, isothiazolyl, pyridazinyl, oxazolyl, isoxazolyl, 5-oxo-1,2,4-oxadiazolyl, 5-oxo-1,2,4-thiadiazolyl, 5-thioxo-1,2,4-oxadiazolyl, 2-oxo-1,2,3,5-oxathiadiazolyl, whereby such rings may be substituted with lower alkyl, lower alkenyl, amino, amino-lower alkyl, halogen, hydroxy, lower alkoxy, trifluoromethoxy, trifluoromethyl, carboxyl, carboxamidyl, thioamidyl, amidinyl, lower alkoxy-carbonyl, cyano, hydroxy-lower alkyl, lower alkyl-oxy-lower alkyl or another heteroaryl- or heterocyclyl-ring (e.g.[7]). The expression aryl represents unsubstituted as well as mono-, di- or tri-substituted aromatic rings with 6 to 10 carbon atoms like phenyl or naphthyl rings which may be substituted with aryl, halogen, hydroxy, lower alkyl, lower alkenyl, lower alkynyl, lower alkoxy, lower alkenyloxy, lower alkynyl-lower alkyl-oxy, lower alkenylen, lower alkylenoxy or lower alkylendioxy forming with the phenyl ring a five- or six-membered ring, hydroxy-lower alkyl, hydroxy-lower alkenyl, hydroxy-lower alkyl-lower alkynyl, lower alkyloxy-lower alkyl, lower alkyloxy-lower alkyloxy, trifluoromethyl, trifluoromethoxy, cycloalkyl, hydroxy-cycloalkyl, heterocyclyl, heteroaryl.

The expression pharmaceutically acceptable salts encompasses either salts with inorganic acids or organic acids like hydrohalogenic acids, e.g. hydrochloric or hydrobromic acid; sulfuric acid, phosphoric acid, nitric acid, citric acid, formic acid, acetic acid, maleic acid, tartaric acid, methylsulfonic acid, p-toluolsulfonic acid and the like or in case the compound of formula I is acidic in nature with an inorganic base like an alkali or earth alkali base, e.g. sodium hydroxide, potassium hydroxide, calcium hydroxide and the like.

The compounds of the general formula I might have one or more asymmetric carbon atoms and may be prepared in form of optically pure enantiomers or diastereomers, mixtures of enantiomers or diastereomers, diastereomeric racemates, mixtures of diastereomeric racemates and also in the meso-form. The present invention encompasses all these forms. Mixtures may be separated in a manner known per se, i.e. by column chromatography, thin layer chromatography, HPLC or crystallization.

Because of their ability to inhibit the endothelin binding, the described compounds of the general formula I and their pharmaceutically acceptable salts may be used for treatment of diseases which are associated with an increase in vasoconstriction, proliferation or inflammation due to endothelin. Examples of such diseases are hypertension, coronary diseases, cardiac insufficiency, renal and myocardial ischemia, renal failure, cerebral ischemia, dementia, migraine, subarachnoidal hemorrhage, Raynaud's syndrome, portal hypertension, and pulmonary hypertension. They can also be used for the treatment or prevention of atherosclerosis, restenosis after balloon or stent angioplasty, inflammation, stomach and duodenal ulcer, cancer, prostatic hypertrophy, erectile dysfunction, hearing loss, amaurosis, chronic bronchitis, asthma, gram negative septicemia, shock, sickle cell anemia, glomerulonephritis, renal colic, glaucoma, therapy and prophylaxis of diabetic complications, complications of vascular or cardiac surgery or after organ transplantation, complications of cyclosporin treatment, pain, hyperlipidemia as well as other diseases presently known to be related to endothelin.

These compositions may be administered in enteral or oral form e.g. as tablets, dragees, gelatine capsules, emulsions, solutions or suspensions, in nasal form like sprays or rectally in form of suppositories. These compounds may also be administered intramuscularly, parenterally or intraveneously, e.g. in form of injectable solutions.

These pharmaceutical compositions may contain the compounds of formula I as well as their pharmaceutically acceptable salts in combination with inorganic and/or organic excipients which are usual in the pharmaceutical industry like lactose, maize or derivatives thereof, talcum, stearinic acid or salts of these materials.

For gelatine capsules vegetable oils, waxes, fats, liquid or half-liquid polyols may be used. For the preparation of solutions and sirups e.g. water, polyols, saccharose, glucose can be used. Injectables can be prepared by using e.g. water, polyols, alcohols, glycerin, vegetable oils, lecithin, or liposomes. Suppositories may be prepared by using natural or hydrogenated oils, waxes, fatty acids (fats), liquid or half-liquid polyols.

The compositions may contain in addition preservatives, stability improving substances, viscosity improving or regulating substances, solubility improving substances, sweeteners, dyes, taste improving compounds, salts to change the osmotic pressure, buffer or anti-oxidants.

The compounds of general formula I may also be used in combination with one or more other therapeutically useful substances e.g. α- and β-blockers like phentolamine, phenoxybenzamine, atenolol, propranolol, timolol, metoprolol, carteolol and the like; vasodilators like hydralazine, minoxidil, diazoxide, or flosequinan; calcium-antagonists like diltiazem, nicardipine, nimodipine, verapamil or nifedipine; ACE-inhibitors like cilazapril, captopril, enalapril, lisinopril and the like; potassium channel activators like pinacidil; angiotensin II receptor antagonists like losartan, valsartan, irbesartan and the like; diuretics like hydrochlorothiazide, chlorothiazide, acetolamide, bumetanide, furosemide, metolazone or chlortalidone; sympatholitics like methyidopa, clonidine, guanabenz, or reserpine; prostacyclin derivatives like flolan; anti-cholinergic substances and other therapeutics which serve to treat high blood pressure or any cardiac disorders.

The dosage may vary within wide limits but should be adapted to the specific situation. In general the dosage given daily in oral form should be between about 3 mg and about 3 g, preferably between about 10 mg and about 1 g, especially preferred between 5 mg and 300 mg, per adult with a body weight of about 70 kg. The dosage should be administered preferably in 1 to 3 doses per day which are of equal weight. As usual children should receive lower doses which are adapted to body weight and age.

Preferred compounds are compounds of general formula I wherein $R^3$ represents phenyl, mono- or di-substituted phenyl substituted with ethoxy, methoxy or chlorine and X represents oxygen, and pharmaceutically acceptable salts thereof.

A second group of preferred compounds of general formula I are those wherein $R^3$ represents phenyl, mono- or di-substituted phenyl substituted with ethoxy, methoxy or chlorine, X represents oxygen and $R^2$ represents —$(CH_2)_m$—Y—$R^a$, and pharmaceutically acceptable salts thereof.

A third group of preferred compounds of general formula I are those wherein $R^3$ represents phenyl, mono- or di-substituted phenyl substituted with ethoxy, methoxy or chlorine, X represents oxygen and $R^2$ represents —$(CH_2)_2$—O—$R^a$, with $R^a$ being heteroaryl, and pharmaceutically acceptable salts thereof.

Another group of preferred compounds are compounds of formula II

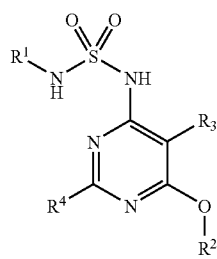

Formula II wherein $R^1$, $R^2$, $R^3$ and $R^4$ are as defined in general formula I above, and pharmaceutically acceptable salts of compounds of formula II.

Also preferred are compounds of formula III

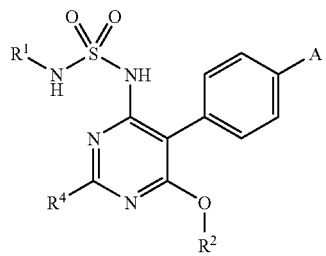

Formula III wherein $R^1$, $R^2$ and $R^4$ are as defined in general formula I above and A represents hydrogen, methyl, ethyl, chlorine, bromine, fluorine, trifluoromethyl, or methoxy, and pharmaceutically acceptable salts of compounds of formula III.

Also preferred are compounds of formula IV

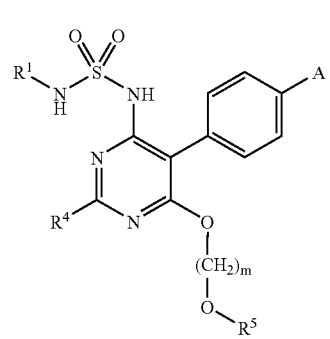

Formula IV wherein $R^1$, $R^4$ and m are as defined in general formula I above and A is as defined in formula III above and $R^5$ represents aryl or heteroaryl, and pharmaceutically acceptable salts of compounds of formula IV.

Another especially preferred group of compounds are compounds of formula V

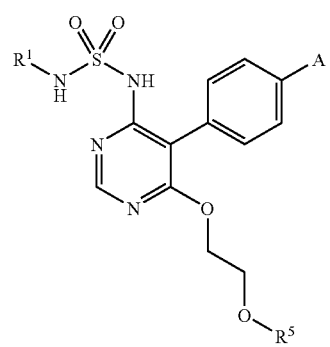

Formula V wherein $R^1$ is as defined in general formula I above, A is as defined in formula III above and $R^5$ represents aryl or heteroaryl, and pharmaceutically acceptable salts of compounds of formula V.

Especially preferred compounds among the group of compounds of formula V are those wherein $R^5$ represents substituted pyrimidine, and pharmaceutically acceptable salts thereof.

Another group of preferred compounds are compounds of general formula I, wherein $R^1$ represents $CH_3$—O—$CH_2CH_2$—, $R^6$ represents hydrogen and $R^2$, $R^3$, and $R^4$ are as defined in general formula I, and pharmaceutically acceptable salts of compounds thereof.

Another group of preferred compounds are compounds of formula V wherein $R^1$ represents $CH_3$—O—$CH_2CH_2$—, A is as defined in formula III above and $R^5$ represents aryl, or heteroaryl, and pharmaceutically acceptable salts of compounds of formula V Particularly preferred compounds are:

2-Methoxy-ethanesulfamic acid [6-[2-(5-bromo-pyrimidin-2-yloxy)-ethoxy]-5-(2-chloro-5-methoxy-phenoxy)-pyrimidin4-yl]-amide;

2-Methoxy-ethanesulfamic acid {5-(4-bromophenyl)-6-[2-(5-bromopyrimidin-2-yloxy)-ethoxy]-pyrimidin4-yl}amide;

2-Methoxy-ethanesulfamic acid {5-(4-bromophenyl)-6-[2-(5-methylsulfanyl-pyrimidin-2-yloxy)-ethoxy]-pyrimidin-4-yl}-amide;

2-Methoxy-ethanesulfamic acid {5-(4-bromophenyl)-6-[2-(5-methoxypyrimidin-2-yloxy)-ethoxy]-pyrimidin-4-yl}-amide.

Compounds of the general formula I of the present invention can be prepared according to the general sequence of reactions outlined below. For simplicity and clarity reasons sometimes only parts of the synthetic possibilities which lead to compounds of general formula I are described. The literature references given in brackets [ ] are set forth at the end of this paragraph.

Possibility A:

The desired compounds of general formula I can be prepared by reacting a compound of the formula 1:

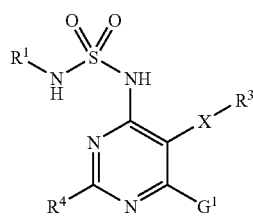

Formula 1 wherein $G^1$ is a reactive residue, preferentially a chlorine atom, and the other symbols are as defined in general formula I above, with a compound of the formula 2:

Formula 2 wherein $R^2$ is as defined in general formula I above, or a salt thereof.

Possibility B:

The compounds of general formula I may also be prepared by reacting a compound of formula 3:

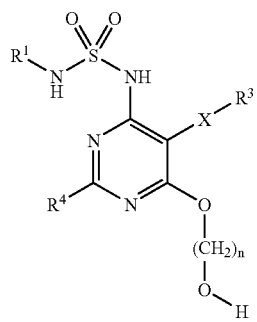

Formula 3 wherein the symbols are the same as defined in general formula I above, or a salt thereof, with a compound of the formula 4:

Formula 4 wherein $G^2$ is a reactive residue, preferentially a halogen atom, and $R^5$ is the same as defined in formula IV above.

Possibility C:

The compounds of general formula I may also be prepared by reacting a compound of the formula 5:

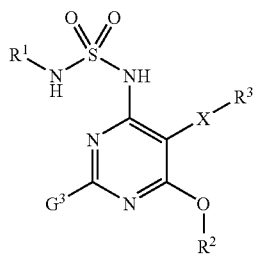

Formula 5

Wherein $G^3$ is a lower alkylsulfonyl group or a phenylsulfonylgroup or a halogen atom, and the other symbols are the same as described in general formula I above, or a salt thereof, with a compound of the formula 6:

Formula 6 wherein $R^{4'}$ represents:

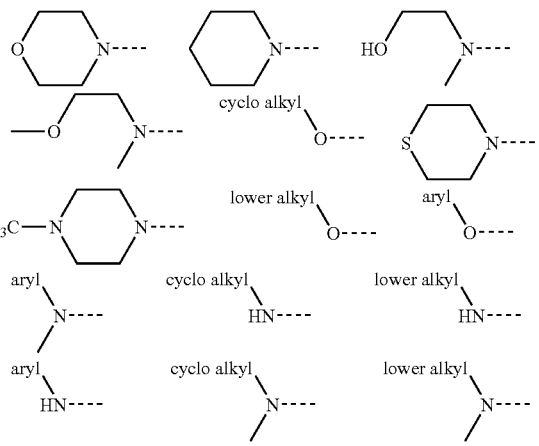

For possibilities A to C see also [5].

In Scheme 1 the synthetic procedure to prepare compounds of the general formula I is depicted by the description of the synthesis of Example 1. The other examples given in this document can be prepared via the same synthetic pathway, adapting the substituents and reaction conditions. The literature references given in [ ] are set forth at the end of this paragraph. The amidines 1 were either commercial or were synthesized applying standard methodology [1] by reaction of the appropriate nitrile with sodium methylate in methanol followed by addition of ammonium chloride. The 2-substituted malonic esters 2 were prepared according to published procedures [2] by reacting dimethylchloromalonate 4 with the appropriate alcohol 3 [9] in acetone and potassium carbonate as base. The compounds 2 were dissolved in methanol, sodium methylate was added, and stirring was continued for about 30 min followed by the addition of an amidine derivative 1. Stirring at ambient temperature was continued for another 8 h. After acidic work up the 4,6-dihydroxypyrimidines 5 could be isolated in yields of 70 to 90% [2]. Compounds 5 or the tautomeric form thereof were transformed into the dichloro derivatives 6 with phosphorus oxychloride in the presence of N,N-dimethylaniline at elevated temperatures (60-120° C.) in yields of 40 to 75% [3]. The dichlorides 6 were reacted with an excess of the appropriate sulfamide potassium salt 7 (prepared as outlined in Scheme 2) in DMSO at r.t. or 40 to 60° C. to give the monochloro-pyrimidines 8 in yields of 70 to 90% either after recrystallization or chromatography. The pyrimidine derivatives 8 are then reacted with ethylene glycol (or another 1-ω-diol, or a mono alcohol) in the presence of a base like potassium tert.-butylate, sodium hydride or sodium at 80-110° C. for 4 to 16 h to give compounds 9 as the first claimed compounds in yields of 50 to 70%. Compound 9 can be further transformed to compounds 11 by reaction with 2-chloro-5-bromopyrimidine 10 (or another suitable pyrimidine or pyridine derivative [16], [17]) in THF/DMF~5/1 at either r.t. or at 50-70° C. in yields of 50-80%.

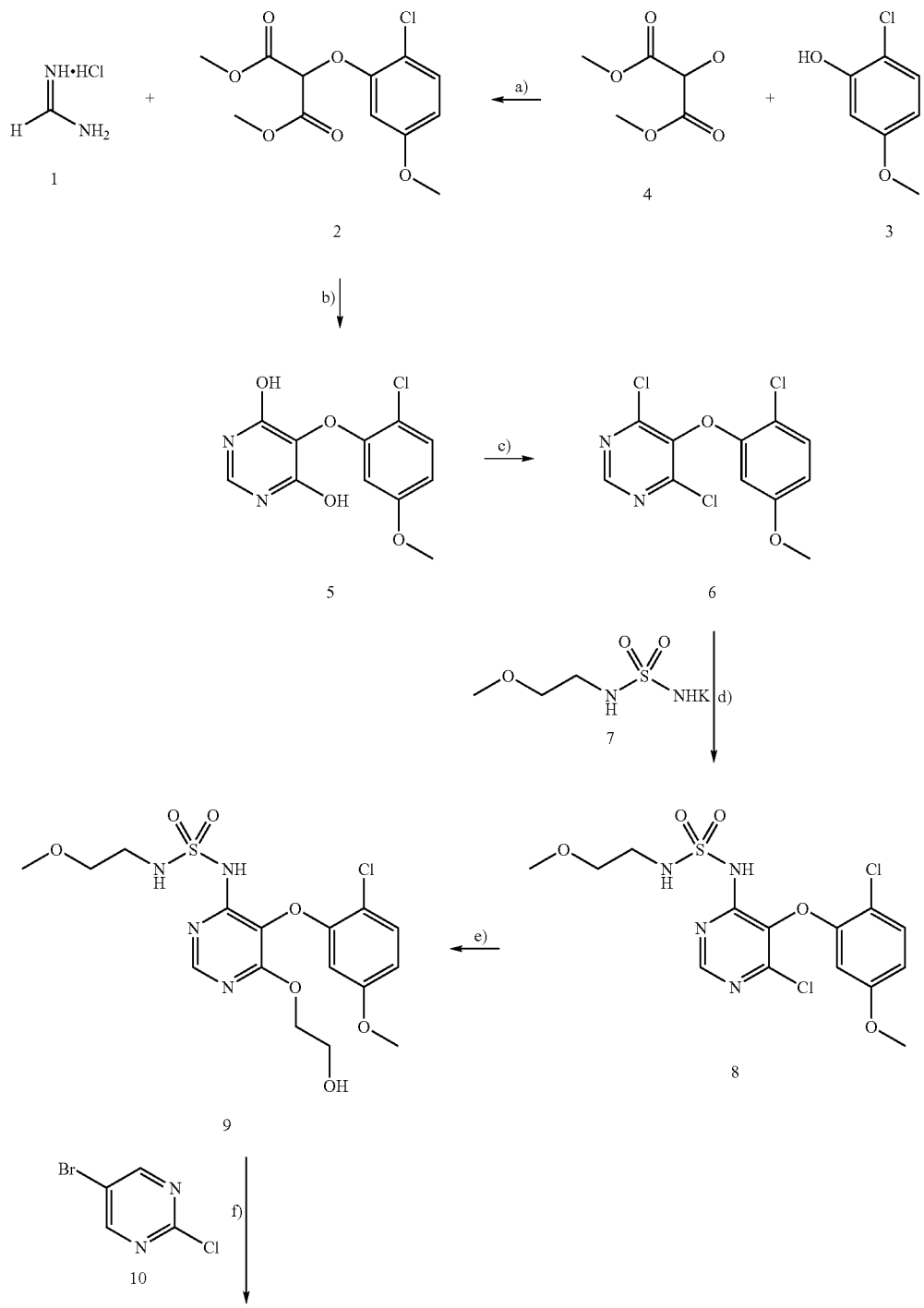

Scheme 1: Exemplified synthesis of Example 1.

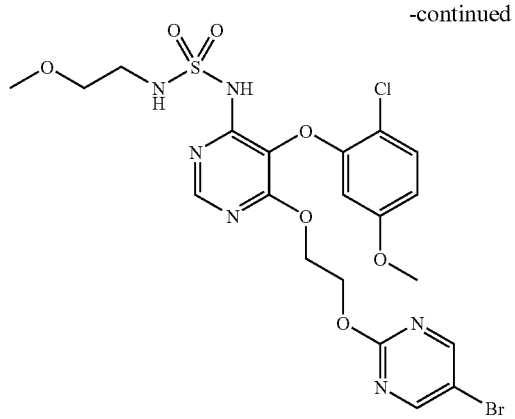
11
a) K$_2$CO$_3$, acetone, reflux; b) NaOMe, MeOH, rt; c) POCl$_3$, N,N-dimethylaniline, 70-130° C.; d) 7, DMSO, rt; e) K-tert.-butylate, ethylene glycol, 75-100° C.; f) NaH, DMF and/or THF, 10, rt to 60° C.
For further experimental descriptions see [1]-[3], [5], [6], [8], [10]-[15] and [20].
Scheme 2: Preparation of the sulfamide moieties. See also [10]-[15], [19] and [20], and the preparation of substituted pyrimidines according to [16] and [17].
a)
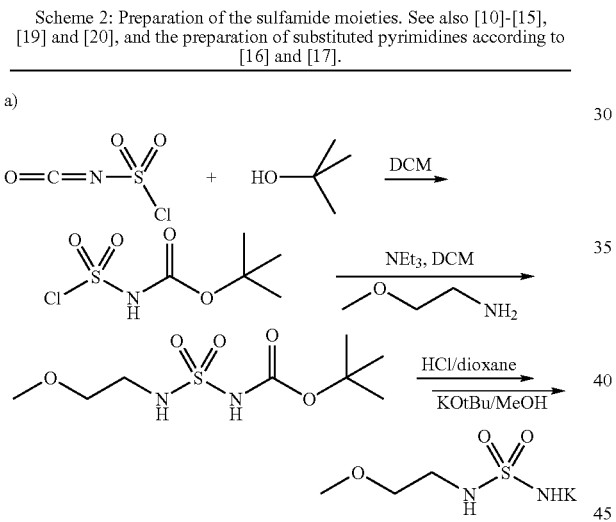
b)
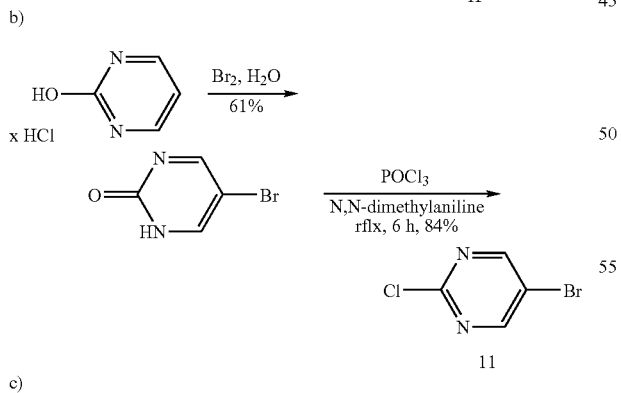
c)
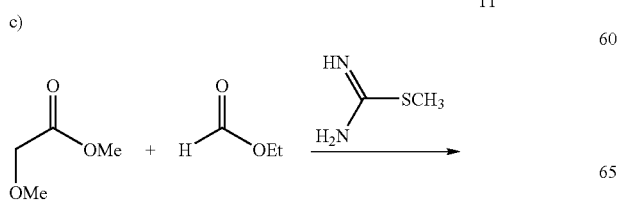
d)
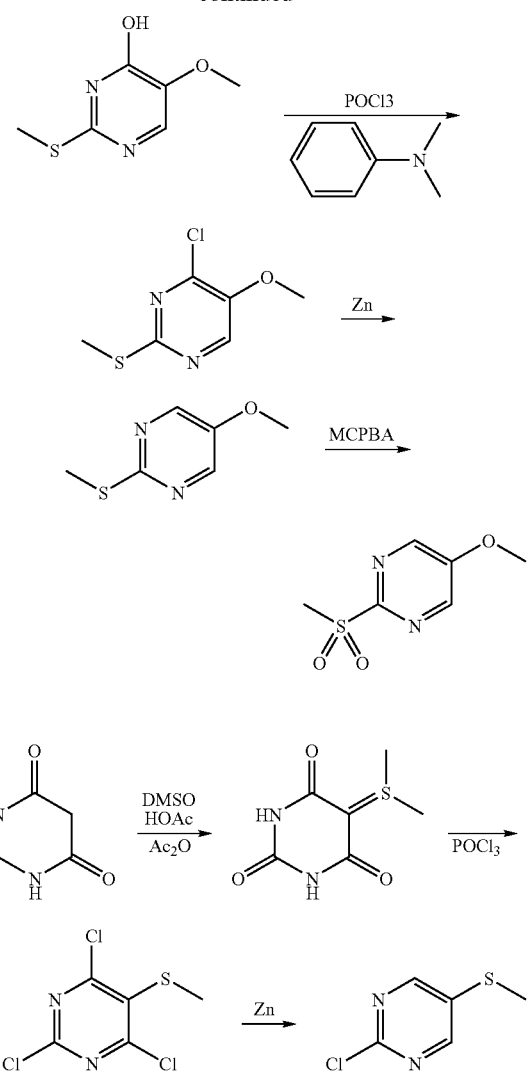

Scheme 3: Preparation of the precursors for the synthesis of compounds of general formula I wherein X represents a bond [5], [18]:

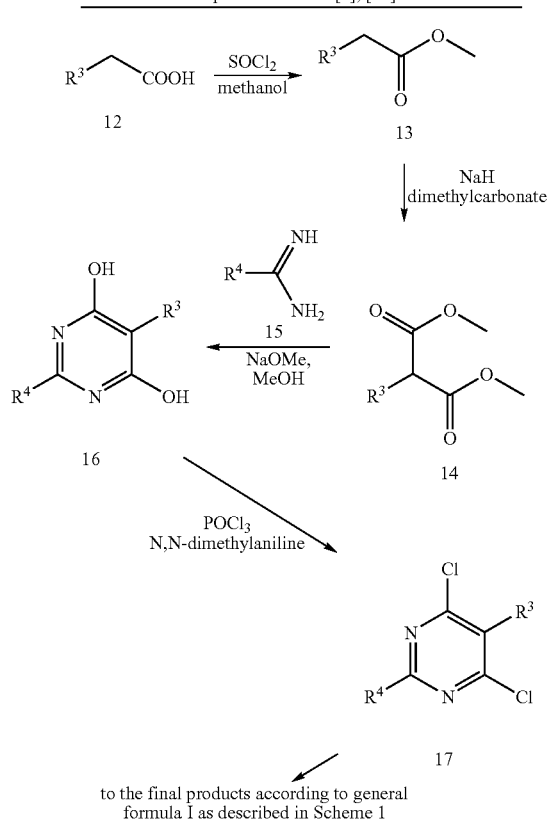

to the final products according to general formula I as described in Scheme 1

In Scheme 3 the symbols represent the same as defined in general formula I above.

[1] W. Göhring, J. Schildknecht, M. Federspiel; *Chimia,* 1996, 50, 538-543.
[2] W. Neidhart, V. Breu, D. Bur, K. Burri, M. Clozel, G. Hirth, M. Müller, H. P. Wessel, H. Ramuz; *Chimia,* 1996, 50, 519-524 and references cited there.
[3] W. Neidhart, V. Breu, K. Burri, M. Clozel, G. Hirth, U. Klinkhammer, T. Giller, H. Ramuz; *Bioorg. Med. Chem. Lett.,* 1997, 7, 2223-2228. R. A. Nugent, S. T. Schlachter, M. J. Murphy, G. J. Cleek, T. J. Poel, D. G. Whishka, D. R. Graber, Y. Yagi, B. J. Keiser, R. A. Olmsted, L. A. Kopta, S. M. Swaney, S. M. Poppe, J. Morris, W. G. Tarpley, R. C. Thomas; *J. Med. Chem.,* 1998, 41, 3793-3803.
[4] J. March; *Advanced Organic Chemistry,* 4$^{th}$ Ed., 1994, p. 499 and references cited there.
[5] EP 0 743 307 A1; EP 0 658 548 B1; EP 0 959 072 A1 (Tanabe Seiyaku)
[6] EP 0 633 259 B1; EP 0 526 708 A1; WO 96/19459 (F. Hoffmann-LaRoche)
[7] for the Synthesis of 5-membered heterocycles see: Y. Kohara et al; *J. Med. Chem.,* 1996, 39, 5228-5235 and references cited there.
[8] EP 0 882 719 A1 (Yamanouchi Pharmaceutical Co., Ltd)
[9] M. Julia, J. de Rosnay, *Chim. Ther.* 1965, 4, 334-343.
[10] E. Cohen, B. Klarberg; *J. Am. Chem. Soc.,* 1962, 84, 1994.
[11] G. Weiss, G. Schulze, *Liebigs Ann. Chem.,* 1969, 729, 40.
[12] R. Graf, *Chem. Ber.,* 1959, 92, 509.
[13] J. A. Kloek, K. L. Leschinsky, *J. Org. Chem.,* 1976, 41, 4028.
[14] R. E. Olson, T. M. Sielecki, et al; *J. Med. Chem.,* 1999; 42, 1178.
[15] R. P. Dickinson, K. N. Dack, et al; *J. Med. Chem.,* 1997; 40, 3442.
[16] D. G. Crosby, R. V. Berthold; *J. Org. Chem.,* 1960; 25; 1916; D. J. Brown, J. M. Lyall, *Aust. J. Chem.* 1964, 17, 794-802; H. C. Koppel, R. H. Springer, R. K. Robins, C. C. Cheng, *J. Org. Chem.* 1962, 27, 3614-3617; S. A. Jacobsen, S. Rodbotten, T. Benneche, *J. Chem. Soc. Perkin Trans* 1, 1999, 3265-3268; C. Maggiali, G. Morini, F. Mossini, *Farmaco, Ed. Sci.* 1988, 43, 277-292; Patent France 1 549 494 (1968) (D. Razavi).
[17] U.S. Pat. No. 4,233,294 1980. (Bayer AG)
[18] E. D. Morgan; *Tetrahedron,* 1967, 23, 1735.
[19] M. J. Tozer, I. M. Buck et al.; *Bioorg. Med. Chem. Lett.,* 1999, 9, 3103. G. Dewynter et al.; *Tetrahedron,* 1993, 49, 65.
[20] WO 02 53557 (Actelion Pharmaceuticals Ltd.)

EXAMPLES

The following examples illustrate the invention. All temperatures are stated in ° C.

List of Abbreviations:

| | |
|---|---|
| Ac$_2$O | actetic anhydride |
| aq. | aqueous |
| CyHex | cyclohexane |
| DBU | 1,8-diazabicyclo[5.4.0]undec-7-en(1,5-5) |
| DCM | dichloromethane |
| DMAP | 4-dimethylaminopyridine |
| DMF | dimethylformamide |
| DMSO | dimethylsulfoxide |
| EA | ethyl acetate |
| Et$_3$N | triethylamine |
| Hex | hexane |
| HV | high vacuum conditions |
| KOtBu | potassium tert. butylate |
| MCPBA | m-chloroperbenzoic acid |
| min | minutes |
| rflx | reflux |
| rt | room temperature |
| THF | tetrahydrofuran |
| t$_R$ | retention time |

The following compounds were prepared according to the procedure described above and shown in Schemes 1 to 3. All compounds were characterized by 1H-NMR (300 MHz) and occasionally by 13C-NMR (75 MHz) (Varian Oxford, 300 MHz; chemical shifts are given in ppm relative to the solvent used; multiplicities: s=singlet, d=doublet, t=triplet; m=multiplet), by LC-MS[1] (Finnigan Navigator with HP 1100 Binary Pump and DAD, column: 4.6×50 mm, Develosil RP Aqueous, 5 μm, 120 A, gradient: 5-95% acetonitrile in water, 1 min, with 0.04% trifluoroacetic acid, flow: 4.5 ml/min) or LC-MS[2] (Waters Micromass; ZMD-platform with ESI-probe with Alliance 2790 HT and DAD 996, column: 2×30 mm, Gromsil ODS4, 3 μm, 120 A; gradient: 0-100% acetonitrile in water, 6 min, with 0.05% formic acid, flow: 0.45 ml/min), t$_R$ is given in min; by TLC (TLC-plates from Merck, Silica gel 60 F$_{254}$) and occasionally by melting point.

Example 1

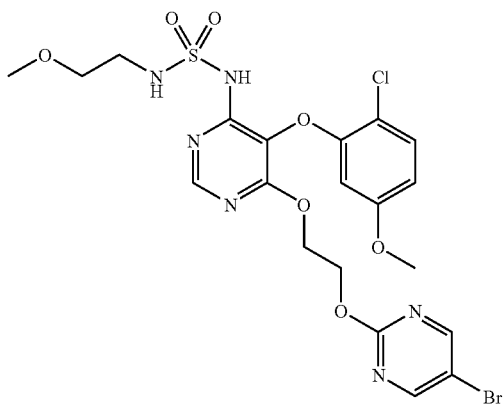

a) To a suspension of K$_2$CO$_3$ (49.3 g) in acetone (100 ml) a solution of 2-chloro-5-methoxy-phenol (37.7 g, boiling point 83-86° C., 13 mbar, [9]) was added dropwise at 40° C. The dropwise addition of dimethyl chloromalonate (43.6 g) in acetone (100 ml) followed. The mixture was refluxed for 16 h before the solvent was removed under reduced pressure. The residue was taken up in water (400 ml) is and extracted twice with DCM (400 ml). The organic extracts were dried over MgSO$_4$ and evaporated. Upon treatment of the oily residue with diethyl ether, the product crystallised. The crystals were collected, washed with a mixture of diethyl ether and hexane and dried to give 2-(2-chloro-5-methoxy-phenoxy)-malonic acid dimethyl ester (53.73 g) as white crystals. $^1$H-NMR(CDCl$_3$): 3.76(s, 3H), 3.86(s, 6H), 5.20(s, 1H), 6.53-6.58(m, 2H), 7.24-7.29(m, 1H).

b) A solution of 2-(2-chloro-5-methoxy-phenoxy)-malonic acid dimethyl ester (10 g) in methanol (100 ml) was added dropwise at 0° C. to a solution of NaOMe (5.6 g) in methanol (250 ml). The solution was stirred at rt for 2 h before formamidine hydrochloride (3.347 g) was added. The mixture was stirred at rt for 72 h. The solvent was removed under reduced pressure and the remaining residue was treated with 2N aq. HCl (150 ml). After stirring for 1 h the solid material was collected, washed with water and dried to give 5-(2-chloro-5-methoxy-phenoxy)-pyrimidine-4,6-diol (8.65 g) as a white powder. $^1$H-NMR(D$_6$-DMSO): 3.65(s, 3H), 6.23, d, J=2.7, 1H), 6.58(dd, J=2.7, 8.8, 1H), 7.33(d, J=8.8, 1H), 8.07(s, 1H), 12.3(s br, 2H).

c) To a solution of N,N-dimethylaniline (7.5 ml) in POCl$_3$ (75 ml) 5-(2-chloro-5-methoxy-phenoxy)-pyrimidine-4,6-diol (8.65 g) was added in portions. The dark red to brown solution was heated to 120° C. and stirred for 3 h. The mixture was cooled and the excess of POCl$_3$ was evaporated. The residue was treated with ice-water (400 ml) and then extracted twice with EA (200 ml). The organic phase was washed with water and evaporated. The crude product was purified by column chromatography on silica gel eluting with heptane:EA 7:3. The isolated product was suspended in methanol, filtered, washed with methanol, diethyl ether/hexane and dried to give 4,6-dichloro-5-(2-chloro-5-methoxy-phenoxy)-pyrimidine (8.23 g) as a pale yellow powder. $^1$H-NMR(CDCl$_3$): 3.72(s, 3H), 6.05(d, J=2.7, 1H), 6.62(dd, J=2.7, 8.8, 1H), 7.38(d, J=8.8, 1H), 8.69(s, 1H).

d) Tert.-butanol (5.56 g) is added dropwise to a solution of chlorosulfonyl isocyanate (10.61 g) in DCM (40 ml) while the temperature is maintained at 0-4° C. Stirring is continued for 30 min at 0° C. before an ice-cold solution of 2-methoxy-ethylamine (5.63 g) and triethylamine (8.35 g) in DCM (80 ml) is added dropwise while the temperature of the mixture is kept at 0-2° C. Then the mixture is warmed to rt and stirring is continued for 72 h. The mixture is washed twice with water (15 ml) and the aqueous phase was back extracted with DCM (50 ml). The organic phase was dried over MgSO$_4$ and evaporated. The remaining oil was dried under high vacuum before it was dissolved in 2-propanol (200 ml). The solution was cooled to –70° C. and then treated with 5-6 N HCl in 2-propanol (80 ml). The mixture was warmed to rt and stirring is continued for 18 h before the solvent was evaporated. The residue was dissolved in methanol (150 ml) and potassium tert.-butylate (8.42 g) was added in portions. The solution was stirred for 10 min and the solvent was evaporated. The remaining residue was dried under high vacuum to give 2-methoxy-ethanesulfamic acid amide potassium salt (15.51 g). $^1$H-NMR(D$_6$-DMSO): 2.88-2.96 (m, 2H), 3.15 (s, 3H), 3.32-3.40(m, 2H); $^{13}$C-NMR(D$_6$-DMSO): 43.7, 58.6, 72.3.

e) A solution of 4,6-dichloro-5-(2-chloro-5-methoxy-phenoxy)-pyrimidine (1.00 g) and 2-methoxyethylsulfamic acid amide potassium salt (1.38 g) in DMSO (15 ml) was stirred at rt for 18 h before it was diluted with a 10% aq. citric acid solution (100 ml) and extracted twice with EA (100 ml). The organic phase was washed twice with water (100 ml), dried over MgSO$_4$ and evaporated. The product crystallised from diethyl ether/hexane. The crystals were collected, washed with additional diethyl ether and dried under high vacuum to give 2-methoxy-ethanesulfamic acid [6-chloro-5-(2-chloro-5-methoxy-phenoxy)-pyrimidin-4-yl]-amide (1.19 g) as a beige powder. LC-MS$^1$: $t_R$=1.02 min, [M+1]$^+$=422.92. $^1$H-NMR(CDCl$_3$): 3.20-3.28(m, 2H), 3.27(s, 3H), 3.44-3.50(m, 2H), 3.72(s, 3H), 5.90-5.96(m br, 1H), 6.18(d, 2.9, 1H), 6.65(dd, 2.9, 8.8, 1H), 7.37(d, 8.8, 1H), 7.91(s br, 1H), 8.54(s, 1H); $^{13}$C-NMR (CDCl$_3$): 44.1, 56.1, 59.1, 70.2, 102.9, 110.0, 114.7, 131.5, 132.2, 151.3, 152.4, 152.8, 153.9, 159.6.

f) To a suspension of 2-methoxy-ethanesulfamic acid [6-chloro-5-(2-chloro-5-methoxy-phenoxy)-pyrimidin-4-yl]-amide (1.17 g) in ethylene glycol (15 ml) was added potassium tert.-butlylate (3.10 g). The resulting clear solution was stirred at 90° C. for 24 h, cooled to rt, diluted with EA (200 ml) and washed with 10% aq. citric acid (150 ml) and water (2×100 ml). The aqueous phase was extracted once more with EA (100 ml). The combined organic phase was dried over MgSO$_4$ and evaporated. The residue was purified by column chromatography on silica gel eluting with hexane:EA 1:3 to give 2-methoxy-ethanesulfamic acid [5-(2-chloro-5-methoxy-phenoxy)-6-(2-hydroxy-ethoxy)-pyrimidin4-yl]-amide (1.03 g) as a colourless glass. LC-MS$^1$: $t_R$=0.89 min, [M+1]$^+$=448.92.

g) NaH (78 mg of a 55% dispersion in mineral oil) was added to a solution of 2-methoxy-ethanesulfamic acid [5-(2-chloro-5-methoxy-phenoxy)-6-(2-hydroxy-ethoxy)-pyrimidin-4-yl]-amide (200 mg) in DMF (6 ml). The mixture was stirred for 5 min before 5-bromo-2-chloro-pyrimidine (172 mg) was added. The mixture was heated to 55° C. and stirred for 3 h, diluted with EA (75 ml) and washed with 10% aq. citric acid solution (50 ml) and water (2×50 ml). The organic phase was evaporated and the residue was purified by chromatography on prep. tlc plates with heptane:EA 1:2 to give 2-methoxy-ethanesulfamic acid [6-[2-

(5-bromo-pyrimidin-2-yloxy)-ethoxy]-5-(2-chloro-5-methoxy-phenoxy)-pyrimidin-4-yl]-amide as a colourless foam. LC-MS[1]: $t_R$=1.07 min, [M+1]⁺=604.95. ¹H-NMR (CDCl₃): 3.23(d, 5.3, 2H), 3.29(s, 3H), 3.50(t, 4.7, 2H), 3.67(s, 3H), 4.52-4.54(m, 2H), 4.68-4.74(m, 2H), 5.93(t, 5.9, 1H), 6.24(d, 2.3, 1H), 6.52(dd, 2.9, 8.8, 1H), 7.22(d, 8.8, 1H), 7.58(s, 1H), 8.32(s, 1H), 8.45(s, 2H).

Example 2

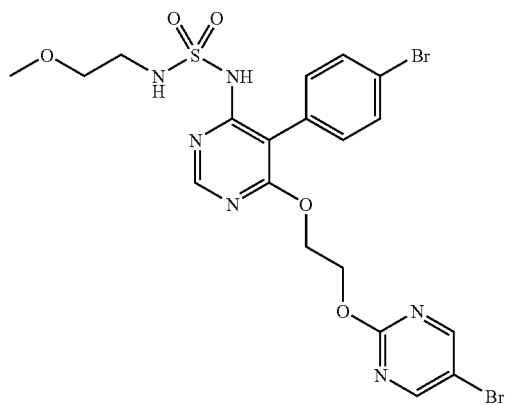

a) To a solution of 4-bromophenylacetic acid (50 g) in methanol (250 ml) thionyl chloride (34.2 ml) was added dropwise while the temperature of the reaction mixture was kept at 0-5° C. Upon complete addition the cooling is removed and the mixture is allowed to warm to rt. Stirring was continued for 75 min before the solvent was removed in vacuo. The yellow oil was dissolved in benzene and evaporated. The residue was dissolved in EA, washed with water, brine, 2 N aq. Na₂CO₃, and brine. The organic phase was dried over MgSO₄ and evaporated and dried under high vacuum at 85° C. for 30 min to give 4-bromophenylacetic acid methyl ester (52.4 g) as a yellow oil. ¹H-NMR (D₆-DMSO): 3.60(s, 3H), 3.67(s, 2H), 7.22(d, 8.5, 2H), 7.50(d, 8.5, 2H).

b) At 40° C. a solution of 4-bromophenylacetic acid methyl ester (52 g) in THF (100 ml) was carefully added over a period of 40 min to a suspension of NaH (15.6 g) in dry THF (450 ml). Stirring was continued for 70 min without heating and the temperature dropped to 27° C. The evolution of gas had stopped before dimethylcarbonate (76.42 ml) was added dropwise while the temperature of the mixture was maintained at 29-31° C. Stirring was continued for 22 h at rt. The mixture was cooled to −10° C. and then carefully neutralized to pH 6-7 with aq. HCl before bulk of the THF was removed in vacuo. The residue was dissolved in EA (700 ml), washed three times with 1 N aq. HCl and once with brine, dried over MgSO₄. Most of the EA was evaporated before hexane was added. The product crystallised over night at 4° C. The crystals were collected, washed with hexane and dried to give 2-(4-bromophenyl)-malonic acid dimethyl ester (45.9 g) as pale yellow crystals. ¹H-NMR(D₆-DMSO): 3.66(s, 6H), 5.07(s, 1H), 7.30-7.34(m, 2H), 7.55-7.59(m, 2H).

c) A solution of 2-(4-bromophenyl)-malonic acid dimethyl ester (11.73 g) in methanol (100 ml) was added at 0° C. to a solution of sodium (2.83 g) in methanol (100 ml). The mixture was stirred for 18 h at rt before formamidine hydrochloride (4.10 g) was added. The suspension was stirred at rt for 4 h. The solvent was removed and the residue was suspended in 10% aq. citric acid (100 ml) and stirred for 10 min. The white precipitate was collected, washed with 10% aq. citric acid, water, evaporated three times from CyHex and dried under high vacuum at 40° C. to give 5-(4-bromophenyl)-pyrimidine-4,6-diol (9.90 g) as a pale beige powder. LC-MS: $t_R$=2.75 min, [M+H]⁺ =222.96, [M−H]⁻=220.92. ¹H-NMR(D₆-DMSO): 7.43-7.48(m, 2H), 7.50-7.55(m, 2H), 8.13(s, 1H), 12.1(s br, 2H).

d) To a suspension of 5-(4-bromophenyl)-pyrimidine-4,6-diol (9.90 g) in POCl₃ (130 ml) was carefully added N,N-dimethylaniline (13.5 ml). The mixture was heated to 130° C. for 2 h. The dark brown solution was evaporated and the residue was poured into ice/water. The suspension was diluted with 2 N HCl and water and stirred for 20 min. The precipitate was collected and washed with water. The solid material was dissolved in EA, washed with 1 N aq. HCl and brine. The organic phase was dried over MgSO₄ and evaporated. The material was further purified by column chromatography on silica gel eluting with hexane:EA 95:5 to 1:1 followed by crystallisation from hexane/EA at −20° C. to give 4,6-dichloro-5-(4-bromophenyl)-pyrimidine (8.3 g) as pale yellow crystals. ¹H-NMR(D₆-DMSO): 7.39-7.44(m, 2H), 7.72-7.76(m, 2H), 8.94(s, 1H).

e) A solution of 4,6-dichloro-5-(4-bromophenyl)-pyrimidine 1.79 mg) and 2-methoxyethanesulfamic acid amide potassium salt (4.54 g, Example 1) in DMF (25 ml) was stirred at rt for 24 h before bulk of the solvent was removed in vacuo. The residue was treated with 10% aq. citric acid. The suspension was filtered, and the mother liquor was extracted twice with EA. The organic phase was evaporated and combined with the solid material collected earlier. The crude product was purified by column chromatography on silica gel eluting with DCM containing 4% of methanol to give 2-methoxyethanesulfamic acid [6-chloro-5-(4-bromophenyl)-pyrimidin-4-yl]-amide (640 mg) as a beige foam. LC-MS²: $t_R$=4.46 min, [M+1]⁺ =422.93, [M−1]⁻=420.82.

f) To a suspension of 2-methoxyethanesulfamic acid [6-chloro-5-(4-bromophenyl)-pyrimidin-4-yl]-amide (640 mg g) in ethylene glycol (10 ml) was added potassium tert.-butylate (1.70 g) in three portions. The resulting clear solution was stirred for 17 h at 90° C., cooled to rt, diluted with EA (200 ml) and washed with 10% aq. citric acid (150 ml) and water (2×100 ml). The aqueous phase was extracted once more with EA (100 ml). The combined organic phase was evaporated. The residue was purified by column chromatography on silica gel eluting with hexane:EA 2:1 to 3:1 to give 2-methoxy-ethanesulfamic acid [5-(4-bromophenyl)-6-(2-hydroxyethoxy)-pyrimidin-4-yl]-amide (533 mg) as a colourless foam. LC-MS²: $t_R$=3.81 min, [M+3(Br isotope)]⁺=449.05, [M−1+2(Br isotope)]⁻ =446.94. ¹H-NMR(CDCl₃): 3.14-3.22(m, 2H), 3.30(s, 3H), 3.47-3.53(m, 2H), 3.82-3.88(m, 2H), 4.47-4.52(m, 2H), 5.98-6.06(m br, 1H), 7.17-7.22(m, 2H), 7.62-7.68(m, 2H), 8.49(s, 1H).

g) NaH (59 mg 55% in mineral oil) was added to a solution of 2-methoxy-ethanesulfamic acid [5-(4-bromophenyl)-6-(2-hydroxyethoxy)-pyrimidin-4-yl]-amide (150 mg) in DMF (4 ml). The mixture was stirred for 5 min before 5-bromo-2-chloropyrimidine (130 mg) was added. The mixture was heated to 55° C. and stirred for 3 h, diluted with EA (75 ml) and washed with 10% aq. citric acid solution (50 ml) and water (2×50 ml). The organic phase was evaporated and the residue was purified by chromatography on prep. tic plates with EA 1 to give 2-methoxy-ethanesulfamic acid {5-(4-bromophenyl)-6-[2-(5-bromopyrimidin-2-yloxy)- ethoxy]-pyrimidin-4-yl}-amide (91 mg) as a beige foam. LC-MS$^1$: $t_R$=0.97 min, [M+1+2 (Br isotope)]$^+$=605.00, LC-MS$^2$: $t_R$=4.97 min, [M+1]$^+$=602.91, [M−1]$^-$=601.09

Example 3

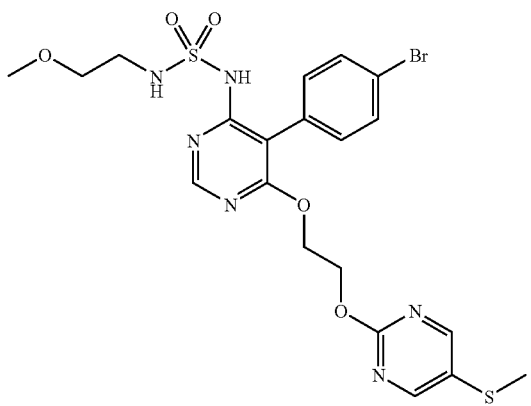

2-Methoxy-ethanesulfamic acid {5-(4-bromophenyl)-6-[2-(5-methylsulfanyl-pyrimidin-2-yloxy)-ethoxy]-pyrimidin-4-yl}-amide was obtained in analogy to Example 2 starting from 2-methoxy-ethanesulfamic acid [5-(4-bromophenyl)-6-(2-hydroxyethoxy)-pyrimidin-4-yl]-amide (Example 2) and 2-chloro-5-methylsulfanyl-pyrimidine as a colourless foam. LC-MS$^2$: $t_R$=4.88 min, [M+3(Br isotope)]$^+$=572.87, [M−1+2(Br isotope)]$^-$=571.12. $^1$H-NMR(CDCl$_3$): 2.00(s, 3H), 2.69-2.73(m, 2H), 2.82(s, 3H), 3.00-3.07(m, 2H), 4.11-4.20(m, 2H), 4.23-4.31(m, 2H), 5.60(s br, 1H), 6.67-6.74(m, 2H), 7.06-7.13(m, 2H), 7.99(s, 2H), 8.00(s, 1H).

Example 4

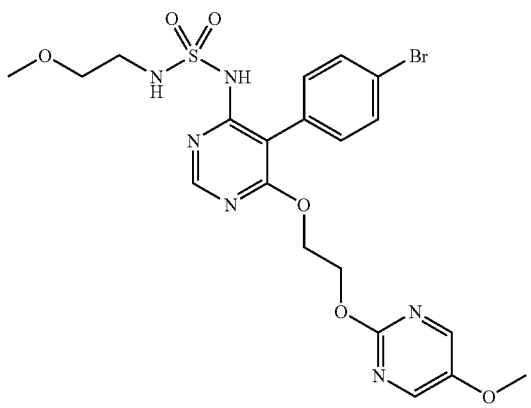

2-Methoxy-ethanesulfamic acid {5-(4-bromophenyl)-6-[2-(5-methoxypyrimidin-2-yloxy)-ethoxy]-pyrimidin-4-yl}-amide was obtained in analogy to Example 2 starting from 2-methoxy-ethanesulfamic acid [5-(4-bromophenyl)-6-(2-hydroxyethoxy)-pyrimidin-4-yl]-amide (Example 2) and 2-methanesulfonyl-5-methoxypyrimidine as a white solid. LC-MS$^2$: $t_R$=4.56 min, [M+3(Br isotope)]$^+$=556.97, [M−1+2(Br isotope)]$^-$=555.05. $^1$H-NMR(CDCl$_3$): 3.14-3.20(m, 2H), 3.28(s, 3H), 3.46-3.51 (m, 2H), 3.87(s, 3H), 4.56-4.60 (m, 2H), 4.68-4.73(m, 2H). 6.06(s br, 1H), 7.13-7.18(m, 2H), 7.52-7.56(m, 2H), 8.15(s, 2H), 8.47(s, 1H).

The invention claimed is:
1. A compound of the general formula I,

General Formula I

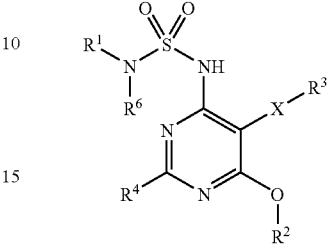

wherein
R$^1$ represents lower alkyl-O—(CH$_2$)$_n$—, cycloalkyl-O—(CH$_2$)$_n$—, cycloalkyl-CH$_2$—O—(CH$_2$)$_n$—;
R$^2$ represents —CH$_3$; R$^a$—Y—(CH$_2$)$_m$—;
R$^3$ represents aryl; heteroaryl;
R$^4$ represents hydrogen; trifluoromethyl; lower alkyl; lower alkyl-amino; lower alkyloxy; lower alkyloxy-lower alkyloxy; hydroxy-lower alkyloxy; lower alkyl-sulfinyl; lower alkylthio; lower alkylthio-lower alkyl; hydroxy-lower alkyl; lower alkyloxy-lower alkyl; hydroxy-lower alkyloxy-lower alkyl; hydroxy-lower alkyl-amino; lower alkylamino-lower alkyl; amino; di-lower alkylamino; [N-(hydroxy-lower alkyl)-N-(lower alkyl)]-amino; aryl; arylamino; aryl-lower alkylamino; aryl-thio; aryl-lower alkylthio; aryloxy; aryl-lower alkyloxy; aryl-lower alkyl; arylsulfinyl; heteroaryl; heteroaryl-oxy; heteroarylamino; heteroarylthio; heteroaryl-lower alkyl; heteroarylsulfinyl; heterocyclyl; heterocyclyl-lower alkyloxy; heterocyclyloxy; heterocyclylamino; heterocyclyl-lower alkylamino; heterocyclylthio; heterocyclyl-lower alkylthio; heterocyclyl-lower alkyl; heterocyclylsulfinyl; cycloalkyl; cycloalkyloxy; cycloalkyl-lower alkyloxy; cycloalkylamino; cycloalkyl-lower alkylamino; cycloalkylthio; cycloalkyl-lower alkylthio; cycloalkyl-lower alkyl; cycloalkylsulfinyl;
R$^6$ represents hydrogen or methyl;
X represents oxygen; sulfur; —CH$_2$— or a bond;
Y represents a bond, —O—; —NH—; —SO$_2$—NH—; —NH—SO$_2$—NH—; —O—CO—; —CO—O—; —O—CO—NH—; —NH—CO—O—; —NH—CO—NH—;
n represents the integers 2, 3, or 4;
m represents the integers 2, 3, or 4; and
R$^a$ represents aryl, heteroaryl, lower alkyl, cycloalkyl, hydrogen;
and optically pure enantiomers, mixtures of enantiomers, optically pure diastereomers, mixtures of diastereomers, diastereomeric racemates, mixtures of diastereomeric racemates and the meso-forms and pharmaceutically acceptable salts thereof.

2. The compound of claim 1, wherein R$^3$ represents phenyl, mono-or di-substituted phenyl substituted with ethoxy, methoxy or chlorine and X represents oxygen, and pharmaceutically acceptable salts thereof.

3. The compound of claim 1, wherein R$^3$ represents phenyl, mono-or di-substituted phenyl substituted with ethoxy, methoxy or chlorine, X represents oxygen and $R^2$ represents —$(CH_2)_m$—Y—$R^a$, and pharmaceutically acceptable salts thereof.

4. The compound of claim 1, wherein $R^3$ represents phenyl, mono-or di-substituted phenyl substituted with ethoxy, methoxy or chlorine, X represents oxygen and $R^2$ represents —$(CH_2)_2$—O—$R^a$, with $R^a$ being heteroaryl, and pharmaceutically acceptable salts thereof.

5. The compound of claim 1, said compound having formula II

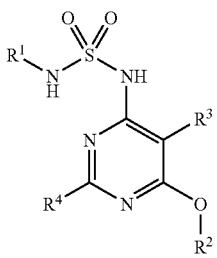

Formula II and pharmaceutically acceptable salts of the compound.

6. The compound of claim 1, said compound having formula III

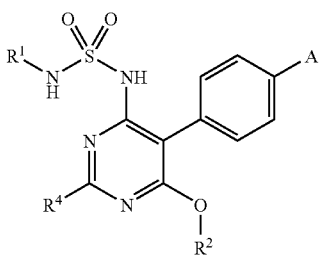

Formula III wherein A represents hydrogen, methyl, ethyl, chlorine, bromine, fluorine, trifluoromethyl or methoxy, and pharmaceutically acceptable salts of the compound.

7. The compound of claim 1, said compound having formula IV

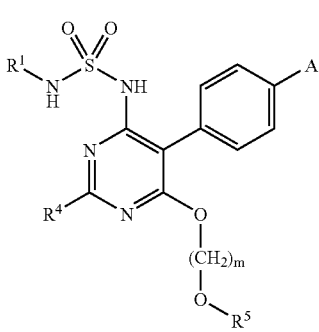

Formula IV wherein A represents hydrogen, methyl, ethyl, chlorine, bromine, fluorine, trifluoromethyl or methoxy, and $R^5$ represents aryl or heteroaryl, and pharmaceutically acceptable salts of the compound.

8. The compound of claim 1, said compound having formula V

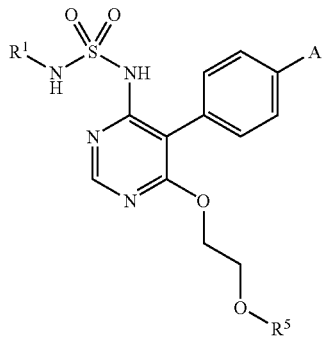

Formula V wherein A represents hydrogen, methyl, ethyl, chlorine, bromine, fluorine, trifluoromethyl or methoxy and $R^5$ represents aryl or heteroaryl, and pharmaceutically acceptable salts of the compound.

9. The compound of claim 8, wherein $R^5$ represents a substituted pyrimidine, and pharmaceutically acceptable salts of the compound.

10. The compound of claim 1, wherein $R^1$ represents $CH_3$—O—$CH_2CH_2$—, and $R^6$ represents and pharmaceutically acceptable salts of the compound.

11. The compound of claim 8, wherein $R^1$ represents $CH_3$—O—$CH_2CH_2$—, and pharmaceutically acceptable salts of the compound.

12. A compound selected from the group consisting of:
  2-Methoxy-ethanesulfamic acid [6-[2-(5-bromo-pyrimidin-2-yloxy)-ethoxy]-5-(2-chloro-5-methoxy-phenoxy)-pyrimidin-4-yl]-amide;
  2-Methoxy-ethanesulfamic acid {5-(4-bromophenyl)-6-[2-(5-bromopyrimidin-2-yloxy)-ethoxy]-pyrimidin-4-yl}-amide;
  2-Methoxy-ethanesulfamic acid {5-(4-bromophenyl)-6-[2-(5-methylsulfanyl-pyrimidin-2-yloxy)-ethoxy]-pyrimidin-4-yl}-amide; and
  2-Methoxy-ethanesulfamic acid {5-(4-bromophenyl)-6-[2-(5-methoxypyrimidin-2-yloxy)-ethoxy]-pyrimidin-4-yl}-amide.

13. A pharmaceutical composition comprising the compound of claim 1 and a pharmaceutically acceptable excipient.

* * * * *